(12) United States Patent
Termechi et al.

(10) Patent No.: US 11,857,569 B1
(45) Date of Patent: Jan. 2, 2024

(54) SALINE-BASED NASAL TREATMENT COMPOSITION

(71) Applicant: Joonem LLC, Chatsworth, CA (US)

(72) Inventors: Eyal Termechi, Woodland Hills, CA (US); Asaf Azaria, Woodland Hills, CA (US)

(73) Assignee: Joonem LLC, Chatsworth, CA (US)

( * ) Notice: Subject to any disclaimer, the term of this patent is extended or adjusted under 35 U.S.C. 154(b) by 0 days.

(21) Appl. No.: 17/848,269

(22) Filed: Jun. 23, 2022

(51) Int. Cl.
| | |
|---|---|
| *A61K 33/14* | (2006.01) |
| *A61P 11/02* | (2006.01) |
| *A61K 35/08* | (2015.01) |
| *A61K 31/355* | (2006.01) |
| *A61K 8/92* | (2006.01) |
| *A61K 8/73* | (2006.01) |
| *A61K 31/047* | (2006.01) |

(52) U.S. Cl.
CPC .............. *A61K 33/14* (2013.01); *A61K 8/731* (2013.01); *A61K 8/92* (2013.01); *A61K 31/047* (2013.01); *A61K 31/355* (2013.01); *A61K 35/08* (2013.01); *A61P 11/02* (2018.01)

(58) Field of Classification Search
None
See application file for complete search history.

(56) References Cited

U.S. PATENT DOCUMENTS

| | | |
|---|---|---|
| 7,115,275 B2 | 10/2006 | Clarot |
| 7,597,901 B2 | 10/2009 | Clarot |
| 7,638,147 B2 | 12/2009 | Chandler |
| 8,053,005 B2 | 11/2011 | Willimann |
| 8,133,502 B2 | 3/2012 | Clarot |
| 8,158,163 B2 | 4/2012 | Willimann |
| 8,778,415 B2 | 7/2014 | Willimann |
| 8,999,406 B2 | 4/2015 | Willimann |
| 9,463,212 B2 | 10/2016 | Willimann |
| 9,943,561 B2 | 4/2018 | Willimann |
| 10,307,452 B2 | 6/2019 | Willimann |
| 2001/0053775 A1* | 12/2001 | Seidel .................. A61K 9/0043 514/649 |
| 2004/0071757 A1* | 4/2004 | Rolf ..................... A61K 9/7061 424/443 |
| 2012/0225137 A1 | 9/2012 | Willimann |

FOREIGN PATENT DOCUMENTS

| | | | | |
|---|---|---|---|---|
| CA | 2910825 | | 10/2014 | |
| CN | 111358730 A | * | 7/2020 | .............. A61K 8/03 |
| CN | 111603478 A | * | 9/2020 | ............ A61K 31/505 |
| WO | WO-9407461 A1 | * | 4/1994 | ............. A61K 8/345 |
| WO | WO-2022061004 A1 | * | 3/2022 | |

OTHER PUBLICATIONS

Google transtion CN 111358730 A, printed 2023 (Year: 2023).*
Google translation CN 111603478 A, printed 2023 (Year: 2023).*
Nozin website: https://www.nozin.com/consumer-store/?gclid=EAlaIQobChMliJ3twZe6-QIVoxx9Ch2NuwMyEAAYASAAEglyIPD_BwE printed Aug. 9, 2022.

* cited by examiner

*Primary Examiner* — Ileana Popa
*Assistant Examiner* — Alissa Prosser
(74) *Attorney, Agent, or Firm* — Kevin Schraven; Anooj Patel; Hankin Patent Law, APC

(57) ABSTRACT

A saline nasal cleansing solution comprising: a water component; a humectant component; a salt component; a cleansing component; a surfactant component; a gelling component; a preservative component; an antioxidant component; and one or more natural extracts; wherein the cleansing component is ppg-26-butanol polyether-26; wherein the humectant component is sorbitol; wherein the salt component is sodium chloride; wherein the surfactant component is PEG-40 hydrogenated castor oil.

2 Claims, 2 Drawing Sheets

SALINE-BASED NASAL TREATMENT COMPOSITION

FIELD OF DISCLOSURE

The present disclosure relates to nasal cleansers used for irrigation and allergy relief through the nasal cavity. More specifically, the present disclosure relates to a composition for a saline gel for cleansing, sterilizing, and soothing the nasal cavity that uses a saline solution as a base, as opposed to an alcohol base.

BACKGROUND

Antiseptics are antimicrobial substances or compounds that are applied to living tissue to reduce the likelihood of infection. Typical examples of antiseptics are phenols and phenol derivatives, diguanides, quinolines, alcohols, peroxides, iodine and iodine derivatives, octenidine dihydrochloride, and quat salts.

While the aforementioned antiseptics are effective at reducing infection, other substances and compounds can act as milder antiseptics. One such example is common saline solution (salt water). Compared to alcohols or peroxides, saline solution less harsh and painful, and is less likely to overly dry out the area to which it is applied. Saline is useful as an antiseptic because it is generally safe to use in wounds, due to its physiological nature. As a result of the safety of using saline, it is a preferred cleanser for wounds. However, there are shortcomings to using saline solution as an antiseptic, such as the fact that it often has consistency and other properties similar to that of plain water.

Even though saline solutions tend to be less harsh than alcohol-based antiseptics, saline solutions tend to be relatively harsh on certain mucus membranes of the nasal passage. Further, currently available saline-based cleansers are liquid and typically are applied via a sprayer. Thus, they tend to be messy and excess saline solution simply drips out of the user's nose.

Therefore, a need exists for a saline-based cleanser that is not harsh, is long lasting, and is not messy to apply.

SUMMARY

The following presents a simplified overview of the example embodiments in order to provide a basic understanding of some embodiments of the example embodiments. This overview is not an extensive overview of the example embodiments. It is intended to neither identify key or critical elements of the example embodiments nor delineate the scope of the appended claims. Its sole purpose is to present some concepts of the example embodiments in a simplified form as a prelude to the more detailed description that is presented hereinbelow. It is to be understood that both the following general description and the following detailed description are exemplary and explanatory only and are not restrictive.

One embodiment of a saline nasal cleaning solution may comprise a water component; a humectant component; a salt component, a cleansing component, and a surfactant component. The cleansing component may be ppg-26-butanol polyether-26. The humectant component may be sorbitol. The salt component may be sodium chloride. The surfactant component may be peg-40 hydrogenated castor oil. The saline nasal cleaning solution may include a gelling component. The gelling component may be hydroxyethyl cellulose. The saline nasal cleaning solution may include a preservative component. The preservative component may be phenoxyethanol. The saline nasal cleaning solution may include an antioxidant component. The antioxidant component may be vitamin e. the saline nasal cleaning solution may include one or more natural extracts. The one or more natural extracts may include aloe extract; honey extract; vanilla extract; peppermint extract; and peppermint oil. The water component may be in an amount from about 70 to about 99 percent by weight based on a total weight of the saline nasal cleaning solution. The water component may be in an amount from about 70 to about 99 percent by weight based on a total weight of the saline nasal cleaning solution. Each of the humectant component; salt component; cleansing component; surfactant component; gelling component; preservative component; antioxidant component; and one or more natural extracts may be in an amount from about 0.1 to about 10 percent by weight based on a total weight of the saline nasal cleaning solution. The saline nasal cleaning solution may include a gelling component, a preservative component, an antioxidant component, and one or more natural extracts; where the water component may be about 71.8% by weight of the total weight of the saline nasal cleaning solution; the humectant component may be sorbitol and may be in an amount of about 10% by weight of the total weight of the saline nasal cleaning solution; the gelling component may be hydroxyethyl cellulose and may be in an amount of about 0.8% by weight of the total weight of the saline nasal cleaning solution; the salt component may be sodium chloride and may be in an amount of about 0.9% by weight of the total weight of the saline nasal cleaning solution; the preservative component may be phenoxyethanol and may be in an amount of about 1% by weight of the total weight of the saline nasal cleaning solution; the cleansing component may be ppg-26-butanol polyether-26 and may be in an amount of about 5% by weight of the total weight of the saline nasal cleaning solution; the surfactant component may be peg-40 hydrogenated castor oil and may be in an amount of about 5% by weight of the total weight of the saline nasal cleaning solution; the antioxidant may be vitamin E and may be in an amount of about 1% by weight of the total weight of the saline nasal cleaning solution; and the one or more natural extracts may be in an amount of about 4.5% by weight of the total weight of the saline nasal cleaning solution. The one or more natural extracts may include an aloe extract; honey extract; vanilla extract; peppermint extract; and peppermint oil; wherein the aloe extract may be in an amount of about 1% by weight of the total weight of the saline nasal cleaning solution; the honey extract may be in an amount of about 1% by weight of the total weight of the saline nasal cleaning solution; the vanilla extract may be in an amount of about 0.5% by weight of the total weight of the saline nasal cleaning solution; the peppermint extract may be in an amount of about 1% by weight of the total weight of the saline nasal cleaning solution. The peppermint extract may be in an amount of about 1% by weight of the total weight of the saline nasal cleaning solution.

Another embodiment may be an applicator, comprising: a proximal end; and a distal end; wherein the distal end comprises a treatment tip; wherein the treatment tip is configured to receive a treatment solution; and wherein the treatment solution comprises a water component; a humectant component; a salt component; a cleansing component; and a surfactant component. The treatment solution may further comprise a gelling component. The applicator may further comprise an inner tube, wherein the inner tube is configured to store the treatment solution and when the inner tube is squeezed, the treatment solution is configured to enter the treatment tip.

One way to apply nasal cleanser may be via the utilization of an applicator device, such as a swab. Some applicator devices that may be used are: plastic bottles with a porous polyethylene applicator tip, a lower reservoir with a plunger on one end of a hollow tube and an applicator tip at the other end of the tube, a two-chambered hollow-stemmed applicator with an internal breakable membrane that, when broken, allows the gel to travel to a cotton applicator tip on one end, or a flocked swab with a polystyrene handle and a flock applicator tip. Other tip types that may be used to apply the gel may be cotton, rayon, polyester, foam, or flocked. In some cases, application could be by use of a finger, or some applicator type not yet in existence.

Still other advantages, embodiments, and features of the subject disclosure will become readily apparent to those of ordinary skill in the art from the following description wherein there is shown and described a preferred embodiment of the present disclosure, simply by way of illustration of one of the best modes best suited to carry out the subject disclosure As it will be realized, the present disclosure is capable of other different embodiments and its several details are capable of modifications in various obvious embodiments all without departing from, or limiting, the scope herein. Accordingly, the drawings and descriptions will be regarded as illustrative in nature and not as restrictive.

BRIEF DESCRIPTION OF THE DRAWINGS

The drawings are of illustrative embodiments. They do not illustrate all embodiments. Other embodiments may be used in addition or instead. Details which may be apparent or unnecessary may be omitted to save space or for more effective illustration. Some embodiments may be practiced with additional components or steps and/or without all of the components or steps which are illustrated. When the same numeral appears in different drawings, it refers to the same or like components or steps.

DETAILED DESCRIPTION

Figure 1:
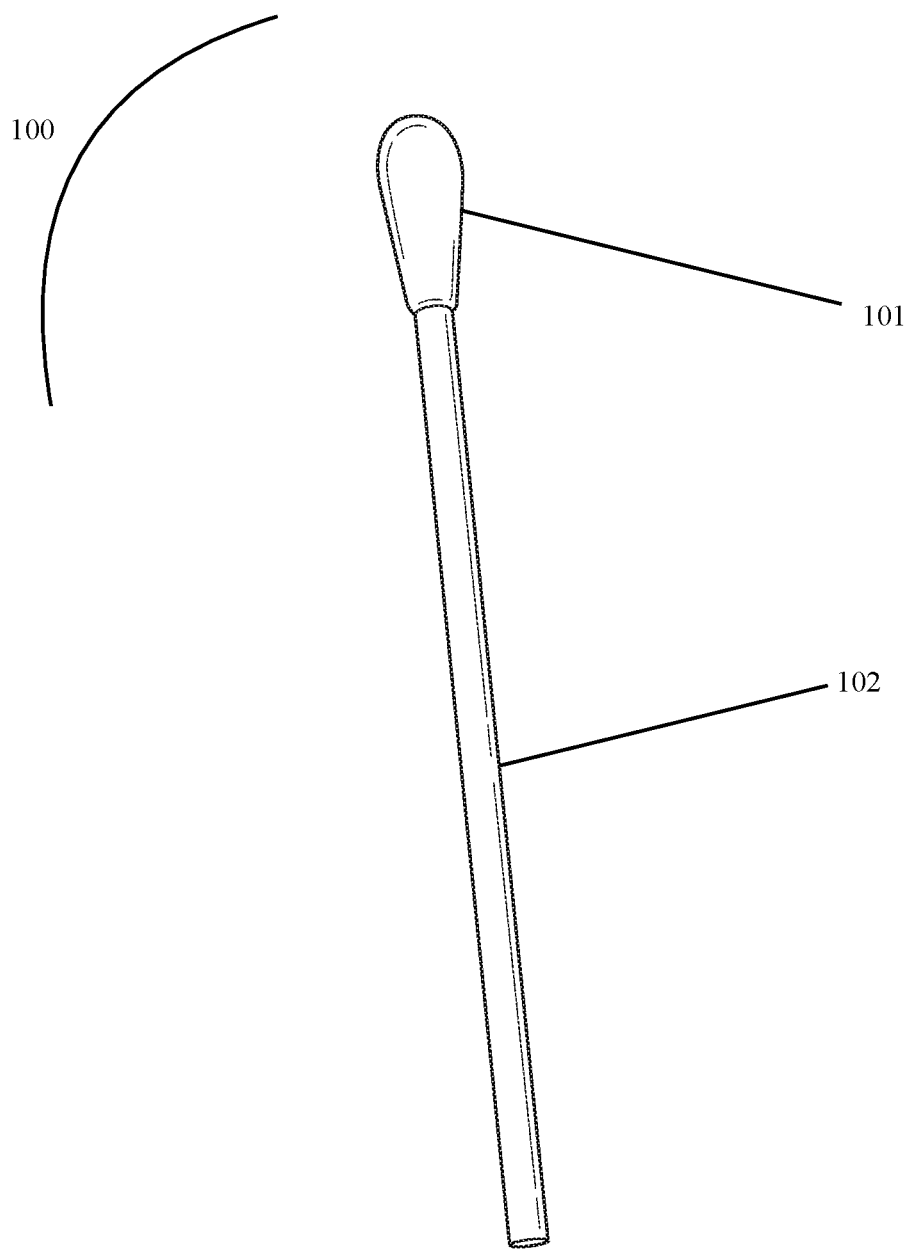
FIG. 1 is an illustration of one embodiment of an applicator for use with a solution.

In the following detailed description of various embodiments, numerous specific details are set forth in order to provide a thorough understanding of various aspects of the embodiments. However, these embodiments may be practiced without some or all of these specific details. In other instances, well-known methods, procedures, and/or components have not been described in detail so as not to unnecessarily obscure aspects of the embodiments.

While multiple embodiments are disclosed, still others will become apparent to those skilled in the art from the following detailed description. As will be realized, these embodiments are capable of modifications in various obvious aspects, all without departing from the spirit and scope of protection. Accordingly, the graphs, figures, and the detailed descriptions thereof, are to be regarded as illustrative in nature and not restrictive. Also, the reference or non-reference to a particular embodiment shall not be interpreted to limit the scope of protection.

In the following description, certain terminology is used to describe certain features of one or more embodiments. For purposes of the specification, unless otherwise specified, the term "substantially" refers to the complete or nearly complete extent or degree of an action, characteristic, property, state, structure, item, or result. For example, in one embodiment, an object that is "substantially" located within a housing would mean that the object is either completely within a housing or nearly completely within a housing. The exact allowable degree of deviation from absolute completeness may in some cases depend on the specific context. However, generally speaking, the nearness of completion will be so as to have the same overall result as if ab solute and total completion were obtained. The use of "substantially" is also equally applicable when used in a negative connotation to refer to the complete or near complete lack of an action, characteristic, property, state, structure, item, or result.

As used herein, the terms "approximately" and/or "about" generally refer to a deviance of within 5% of the indicated number or range of numbers. In one embodiment, the term "approximately" and "about," may refer to a deviance of between 0.0001-40% from the indicated number or range of numbers.

As used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are signify both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Disclosed are components that may be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all embodiments of this application including, but not limited to, steps in disclosed methods. Thus, if there are a variety of additional steps that may be performed it is understood that each of these additional steps may be performed with any specific embodiment or combination of embodiments of the disclosed methods.

The present methods and systems may be understood more readily by reference to the following detailed description of preferred embodiments and the examples included therein and to the Figures and their previous and following description.

Various embodiments are now described with reference to the drawings. In the following description, for purposes of explanation, numerous specific details are set forth in order to provide a thorough understanding of one or more embodiments. It may be evident, however, that the various embodiments may be practiced without these specific details. In other instances, well-known structures and devices are shown in block diagram form to facilitate describing these embodiments. It is to be understood that the methods and systems are not limited to specific methods, specific components, or to particular implementations. It is also to be understood that the terminology used herein is for the purpose of describing particular embodiments only and is not intended to be limiting.

Embodiments of the present disclosure generally relate to the field of antiseptics as nasal cleansers used for irrigation and allergy relief through the nasal cavity. More specifically, the present disclosure relates to a composition for a medicated gel for the intended use of cleansing, sterilizing, and soothing the nasal cavity that uses a saline solution as a base, as opposed to an alcohol base. The method of delivering the gel is mess-free on via delivery by a pre-gelled swab.

FIG. 1 is an illustration of one embodiment of an applicator 100 for use with a solution. As shown in FIG. 1, the applicator device 100 may comprise a tube 102 and a treatment tip 101. In one embodiment the treatment tip 101 may be on a distal end of the applicator 100 and may be substantially any material or structure capable of retaining and/or applying the solution. In some embodiments, the treatment tip 101 may be cotton, rayon, polyester, foam, or flocked. The solution may be substantially similar to one of the solutions described herein below.

In some embodiments, the applicator 100 may further comprise a reservoir portion at a proximal or handle end of the applicator 100. In some embodiments, the tube may allow for the solution to be transferred from the reservoir to the treatment tip 101 upon action (such as squeezing) by a user.

Another embodiment may be of an applicator 100 having a multi-chambered hollow stem. The applicator 100 may comprise a hollow portion and treatment tip 101. In one embodiment, the treatment tip 101 may be on a distal end of the applicator 100 and may be substantially any material or structure capable of retaining and/or applying the solution. In some embodiments, the treatment tip 101 may be cotton, rayon, polyester, foam, or flocked. The solution may be substantially similar to the solution described hereinabove. The user may push more solution preloaded into the hollow portion to the treatment tip 101 by squeezing.

In some embodiments, the hollow stem may comprise two or more chambers each separated by a membrane or other breakable barrier. In one embodiment, the two or more chambers may comprise a first chamber and a second chamber separated by a first membrane or other breakable barrier. The first chamber 315 may be substantially empty, while the second chamber 320 may be filled, partially or completely, with the solution of the present disclosure. In this embodiment, the first chamber may be in fluid communication with the applicator 101 tip. When the membrane or breakable barrier is broken, the solution stored within the second chamber may flow through the first chamber into the treatment tip 101. The treatment tip 101 may have the solution loaded into it so it may then be applied to a user.

In alternate embodiments, the two or more chambers may further comprise a third chamber separated from the second chamber by a second membrane or breakable barrier, such that once the second chamber is partially or completely empties, the user may break the second membrane to allow additional solution to flow from the third chamber, through the second and first chamber, and into the treatment tip. It is understood that substantially any number of chambers may be used, with each preferably separated by a membrane or breakable barrier. One benefit of having multiple chambers is that the user may break chambers in a sequential manner to ensure that an adequate amount of solution may be applied to each desired surface, such as two distinct nostrils.

In some embodiments, the solution may have functions beyond cleansing, sterilizing, and soothing. These additional functions may be based on an additional active substance. Some additional active substances that may be added to the solution may be antiviral compounds, moisturizing compounds, decongestants, and allergy-relief compounds. In another embodiment, the solution is substantially free of both alcohol and peroxide. In one embodiment, the solution is substantially homogeneous.

Another embodiment of the present disclosure is using the solution in a method for cleansing, sterilizing, and soothing a nasal cavity or other mucus membrane comprising the step of administering to the nasal cavity or mucus membrane an applicator, with the applicator containing the solution.

In another embodiment, the applicator may comprise plastic bottles with a polyethylene tip. In another embodiment, the plastic bottles may be configured to house a nasal solution. The solution may be configured to be dispensed via the polyethylene tip. In one embodiment, the solution may have a gel-like consistency such that when applied to a mucus membrane, the solution substantially adheres to the mucus membrane to allow active ingredients of the solution to have a particular desired effect, such as moisturizing, sterilizing, or soothing the mucus membrane. In other embodiments, the solution may have a consistency more similar to water, such that the solution is able to spread out on the surface of the mucus membrane, and if enough solution is applied, allow for cleansing of contaminants on the mucus membrane via the flow of excess solution.

In some embodiments, the solution may be dispensed from the plastic bottles onto a human finger for application inside a nostril. In some embodiments, the solution may be dispensed via a spray from the tips directly into a nostril.

One embodiment of the solution may comprise a water component; a humectant component; a salt component; a cleansing component; and a surfactant component. In some embodiments, the pH of the solution may be adjusted via the use of acidic or basic substances, such as hydrochloric acid and sodium hydroxide. In other embodiments, other acids and/or bases may be used to reach a desired pH for the solution. In some embodiments, the solution may comprise a gelling component. In some embodiments, the solution may comprise a preservative component. In some embodiments, the solution may comprise an antioxidant component. In some embodiments, the solution may comprise one or more natural extracts.

In one embodiment, the water may be in an amount of about 71.8% by weight of the total weight of the solution; the humectant may be sorbitol and may be in an amount of about 10% by weight of the total weight of the solution; the gelling component may be hydroxyethyl cellulose and may be in an amount of about 0.8% by weight of the total weight of the solution; the salt component may be sodium chloride and may be in an amount of about 0.9% by weight of the total weight of the solution; the preservative component may be phenoxyethanol and may be in an amount of about 1% by weight of the total weight of the solution; the cleansing component may be ppg-26-butanol polyether-26 and may be in an amount of about 5% by weight of the total weight of the solution; the surfactant component may be PEG-40 hydrogenated castor oil and may be in an amount of about 5% by weight of the total weight of the solution; the antioxidant may be vitamin E and may be in an amount of about 1% by weight of the total weight of the solution; and the one or more natural extracts may be in an amount of about 4.5% by weight of the total weight of the solution. In some embodiments, the natural extracts may comprise aloe extract; honey extract; vanilla extract; peppermint extract; and peppermint oil.

ppg-26-butanol polyether-26, also called PPG 26 Buteth 26 is an alcohol-based conditioning agent and surfactant that is generally regarded as safe to use on humans.

PEG 40 (Hydrogenated Castor Oil) is the Polyethylene Glycol derivatives of Hydrogenated Castor Oil, and it functions as a surfactant, a solubilizer, an emulsifier, an emollient, a cleansing agent, and a fragrance ingredient when added to cosmetics or personal care product formulations. It is generally regarded as safe for use with humans.

Hydroxyethyl cellulose is a gelling and thickening agent derived from cellulose. It is generally regarded as safe for use with humans.

Phenoxyethanol is a preservative used in cosmetics, perfumes, and toiletries. It is colorless, oily, and has a rose-like odor. It is an ether alcohol that is found in green tea. It is generally regarded as safe for use with humans.

Sorbitol is a sugar alcohol or polyol, and is a water-soluble compound that occurs naturally in many fruits and vegetables. It is generally regarded as safe for use with humans.

One embodiment of the solution may comprise one or more of water; sorbitol; hydroxyethyl cellulose; sodium chloride; phenoxyethanol; ppg-26-butanol polyether-26; PEG-40 hydrogenated castor oil; aloe extract; peppermint oil; vitamin E; honey extract; and vanilla extract. The solution may preferably be substantially free of at least one of alcohol and peroxide. In some embodiments, the solution may comprise no alcohol or peroxide.

Table 1 shows the weight range percentages for the components of one embodiment of the solution.

TABLE 1

| Ingredients | Percent Weight By Composition |
| --- | --- |
| Water | About 70% To About 99% |
| Sorbitol | Up To About 10% |
| Hydroxyethyl Cellulose | Up To About 10% |
| Sodium Chloride | Up To About 10% |
| Phenoxyethanol | Up To About 10% |
| Ppg-26-Butanol Polyether-26 | Up To About 10% |
| PEG-40 Hydrogenated Castor Oil | Up To About 10% |
| Aloe Extract | Up To About 10% |
| Peppermint Oil | Up To About 10% |
| Vitamin E | Up To About 10% |
| Honey Extract | Up To About 10% |
| Vanilla Extract | Up To About 10% |

Table 2 shows weight percentages for the components of a preferred embodiment of the solution.

TABLE 2

| Ingredients | Percent Weight By Composition |
| --- | --- |
| Water | About 71.8 |
| Sorbitol | About 10% |
| Hydroxyethyl Cellulose | About 0.8% |
| Sodium Chloride | About 0.9% |
| Phenoxyethanol | About 1% |
| Ppg-26-Butanol Polyether-26 | About 5% |
| PEG-40 Hydrogenated Castor Oil | About 5% |
| Aloe Extract | About 1% |
| Peppermint Oil | About 1% |
| Vitamin E | About 1% |
| Honey Extract | About 1% |
| Vanilla Extract | About 0.5% |

Phenoxyethanol may act as a preservative in solutions to limit bacterial growth. Peppermint oil, honey extract, and vanilla extract may have antiseptic and antibacterial properties in solutions.

Antiseptics and cleansers used for nasal cleaning are preferably relatively mild because the nasal cavity comprises a mucus membrane and is generally sensitive. Saline solution may have advantages over alcohol or peroxide because saline is generally considered a milder solution. The cleansing effect may also function to reduce the effects of allergies and allergens.

Saline solution may be supplemented with components to further reduce the saline solution's harshness when used as a cleanser and may even act to sooth and hydrate the nasal cavity. In one embodiment, ppg-26-butanol polyether-26, PEG-40 hydrogenated castor oil, vitamin E, and sorbitol may be infused in the saline solution to provide a soothing and hydrating effect when the saline solution is applied to the nasal cavity.

Sorbitol, hydroxyethyl cellulose, and PEG-40 hydrogenated castor oil may cause the saline solution so have a gel-like consistency.

Table 3 shows another embodiment of the ranges of the composition of the present disclosure, list by ingredient type.

TABLE 3

| Ingredients | Percent Weight By Composition (Range) | Purpose |
| --- | --- | --- |
| Water | 22-99.7% | Solvent/Liquid/Water |
| Sorbitol | 0.1-20% | Humectant |
| Hydroxyethyl Cellulose | 0.1-5.0% | Gelling Agent |
| Sodium Chloride | 0.1-5.0% | Salt |
| Phenoxyethanol | 0-5% | Preservative |
| Ppg-26-Butanol Polyether-26 | 0-10% | Cleansing Component |
| PEG-40 Hydrogenated Castor Oil | 0-10% | Surfactant |
| Vitamin E | 0-5.0% | Antioxidant |
| Essential Oils/Natural Extracts (aloe, honey, vanilla, peppermint) | 0-8.0% | Soothing Component |

Other embodiments of the current disclosure may contain soothing components comprising any of the following: aloe vera; calendula; chamomile and blue tansy oil; colloidal oats; evening primrose oil; niacinamide; panthenol; sea buckthorn oil; tea tree oil; rosemary; licorice; green tea; chamomile; and any combination thereof.

Other embodiments of the current disclosure may contain antioxidant components comprising any of the following:

Vitamin C; Vitamin E; niacinamide; retinol; polyphenols; hyaluronic acid; resveratrol; coenzyme Q10; rosemary; tea tree oil; and any combination thereof.

Other embodiments of the current disclosure may contain surfactant components comprising any of the following: sodium lauryl sulphate; ammonium lauryl sulphate; olefin sulfonates; sodium stearate; stearic acid; cetrimonium chloride; stearalkonium chloride; disodium lauryl sulfosuccinate; cocamphocarboxyglycinate; cocoamidopropyl betaine; alpha-olefin sulfonate; and any combination thereof.

Other embodiments of the current disclosure may contain cleansing components comprising any of the following: witch hazel; cucumber and curd; honey; oatmeal; coconut oil; glycerin; hyaluronic acid; ceramides; salicylic acid; tea tree oil; and any combinations thereof.

Other embodiments of the current disclosure may contain preservative components comprising any of the following: phenoxyethanol; benzyl alcohol; sodium benzoate; potassium sorbate; ethylhexylglycerin; triclosan; methylisothiazolinone; methylchloroisothiazolinone; chlorphenesin; chloroxylenol; iodopropynyl butylcarbamate; methyldibromo glutaronitrile; and any combinations thereof.

Other embodiments of the current disclosure may contain salt components comprising sodium chloride; sea salt water; other typically used salts for these applications; and any combinations thereof.

Other embodiments of the current disclosure may contain gelling components comprising any of the following: hydroxyethyl cellulose; guar gum; xanthan gum; beeswax; gelatin; and any combinations thereof.

Other embodiments of the current disclosure may contain humectant components comprising any of the following: glycerin; urea; hyaluronic acid; salicylic acid; alpha hydroxy acids; propylene glycol; honey; sorbitol; and any combinations thereof.

Other embodiments of the current disclosure may contain emollient components comprising any of the following: lanolin; beeswax; mineral oil; patrolatum; shae butter; safflower oil; linoleic acid; oleic acid; lauric acid; stearic acid; and any combinations thereof.

Other embodiments of the current disclosure may contain anti-inflammatory components comprising any of the following: Tea Tree Oil; Rosemary; Chamomile; Aloe Vera; Witch Hazel; Calendula; CBD; Green Tea; Licorice Root; Colloidal Oatmeal; Tiger Grass; Niacinamide; Sodium Chloride; and any combinations thereof.

Other embodiments of the current disclosure may contain natural ingredients or extracts comprising any of the following: beta carotene; green tea extract; licorice; oats; soy; Vitamin C; willow herb; witch hazel; coconut oil; green tee; shea butter; tea tree oil; rosemary; aloe vera; Vitamin B5; dehydroacetic acid; and any combinations thereof.

Figure 2:
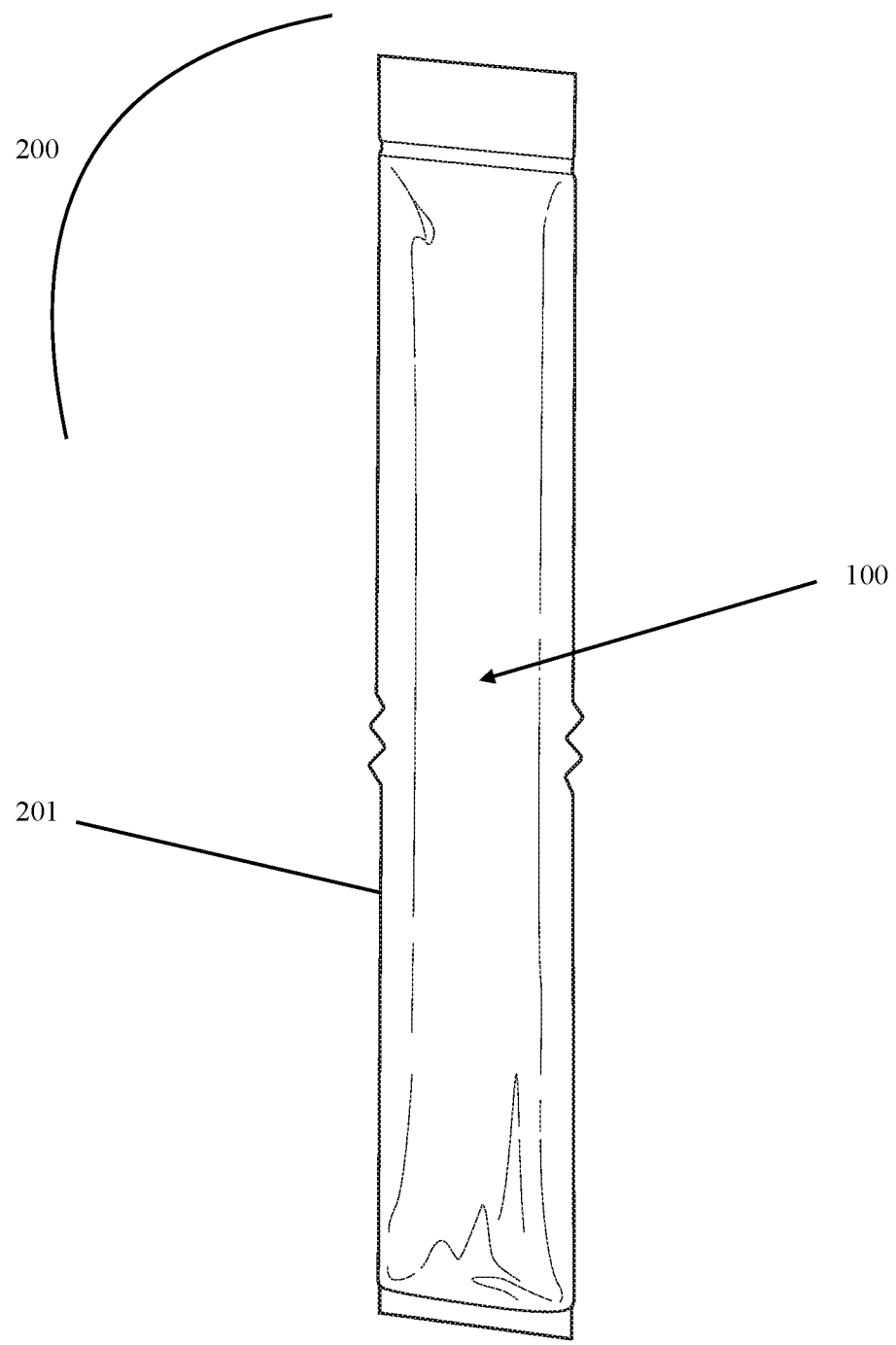
FIG. 2 is an illustration of one embodiment of an applicator encased in a sealed sterile package.

FIG. 2 is an illustration of one embodiment of an applicator 100 encased in a sealed sterile package 200. The sealed sterile package may comprise the applicator 100 and sealed sterile packaging 201. In other embodiments, the applicator 100 may be packaged in a sealed sterile package with the solution pre-applied to the treatment tip 101.

Unless otherwise stated, all measurements, values, ratings, positions, magnitudes, sizes, locations, and other specifications, which set forth in this specification, including in the claims that follow, are approximate, not exact. They are intended to have a reasonable range, which is consistent with the functions to which they relate and with what is customary in the art to which they pertain.

The foregoing description of the preferred embodiment has been presented for the purposes of illustration and description. While multiple embodiments are disclosed, still other embodiments will become apparent to those skilled in the art from the above detailed description, which shows and describes the illustrative embodiments. As will be realized, these embodiments are capable of modifications in various obvious aspects, all without departing from the spirit and scope of the present disclosure. Accordingly, the detailed description is to be regarded. As illustrative in nature and not restrictive. Also, although not explicitly recited, one or more additional embodiments may be practiced in combination or conjunction with one another. Furthermore, the reference or non-reference to a particular embodiment shall not be interpreted to limit the scope of protection. It is intended that the scope of protection not be limited by this detailed description, but by the claims and the equivalents to the claims that are appended hereto.

Except as stated immediately above, nothing which has been stated or illustrated is intended or should be interpreted to cause a dedication of any component, step, feature, object, benefit, advantage, or equivalent to the public, regardless of whether it is or is not recited in the claims.

What is claimed is:

1. A saline nasal cleansing composition comprising:
   a water component;
   a humectant component;
   a salt component;
   a cleansing component;
   a surfactant component; and
   a gelling component, a preservative component, an antioxidant component, and one or more natural extracts;
   wherein said water component is about 71.8% by weight of the total weight of the saline nasal cleaning solution;
   wherein said humectant component is sorbitol and is in an amount of about 10% by weight of the total weight of the saline nasal cleaning solution;
   wherein said gelling component is hydroxyethyl cellulose and is in an amount of about 0.8% by weight of the total weight of the saline nasal cleaning solution;
   wherein said salt component is sodium chloride and is in an amount of about 0.9% by weight of the total weight of the saline nasal cleaning solution;
   wherein said preservative component is phenoxyethanol and is in an amount of about 1% by weight of the total weight of the saline nasal cleaning solution;
   wherein said cleansing component is ppg-26-butanol polyether-26 and is in an amount of about 5% by weight of the total weight of the saline nasal cleaning solution;
   wherein said surfactant component is PEG-40 hydrogenated castor oil and is in an amount of about 5% by weight of the total weight of the saline nasal cleaning solution;
   wherein said antioxidant component is vitamin E and is in an amount of about 1% by weight of the total weight of the saline nasal cleaning solution; and
   wherein said one or more natural extracts is in an amount of about 4.5% by weight of the total weight of the saline nasal cleaning solution.

2. The saline nasal cleansing composition of claim 1, wherein said one or more natural extracts comprise an aloe extract; honey extract; vanilla extract; peppermint extract; and peppermint oil;
   wherein said aloe extract is in an amount of about 1% by weight of the total weight of the saline nasal cleaning solution;

wherein said honey extract is in an amount of about 1% by weight of the total weight of the saline nasal cleaning solution;

wherein said vanilla extract is in an amount of about 0.5% by weight of the total weight of the saline nasal cleaning solution;

wherein said peppermint extract is in an amount of about 1% by weight of the total weight of the saline nasal cleaning solution;

wherein said peppermint oil is in an amount of about 1% by weight of the total weight of the saline nasal cleaning solution.

* * * * *